United States Patent [19]

Kooichi et al.

[11] 4,218,433
[45] Aug. 19, 1980

[54] CONSTANT-RATE ELUTING TABLET AND METHOD OF PRODUCING SAME

[75] Inventors: Yoshida Kooichi, Soka; Shozi Eitoshi; Ootaki Hiroshi, both of Tokyo; Terada Takashi, Yono, all of Japan

[73] Assignee: Nippon Kayaku Kabushiki Kaisha, Tokyo, Japan

[21] Appl. No.: 881,755

[22] Filed: Feb. 27, 1978

[30] Foreign Application Priority Data

Mar. 3, 1977 [JP] Japan .................................. 52-23212

[51] Int. Cl.² .......................... A61K 9/44; A61K 9/28; A61K 9/22; A61K 9/20
[52] U.S. Cl. ..................................... 424/15; 128/260; 424/16; 424/19; 424/21; 424/32; 424/33; 424/35; 427/3
[58] Field of Search .............................. 424/15, 19–22, 424/32, 33, 35; 427/3; 128/260

[56] References Cited

U.S. PATENT DOCUMENTS

| | | | |
|---|---|---|---|
| 216,107 | 6/1879 | Richards | 424/15 |
| 3,113,076 | 12/1963 | Jacobs | 424/15 |
| 3,146,169 | 8/1964 | Stephenson et al. | 424/15 |
| 3,279,995 | 10/1966 | Reid | 424/15 |
| 3,775,537 | 11/1973 | Lehmann et al. | 424/21 |
| 3,845,770 | 11/1974 | Theeuwes et al. | 128/260 |
| 3,917,813 | 11/1975 | Pedersen | 424/20 |
| 4,083,949 | 4/1978 | Benedikt | 424/19 |
| 4,096,238 | 6/1978 | Zaffaroni et al. | 424/15 |

FOREIGN PATENT DOCUMENTS

| | | | |
|---|---|---|---|
| 442266 | 4/1912 | France | 424/15 |
| 1372040 | 10/1974 | United Kingdom | 424/15 |

OTHER PUBLICATIONS

Remington Practice of Pharmacy (1886) pp. 975-977 "Coating Pills."

*Primary Examiner*—Shep K. Rose
*Attorney, Agent, or Firm*—Russell & Nields

[57] ABSTRACT

A tablet formed with a hollow or hollows in its surface and containing a water-soluble component is coated with a coating agent which is insoluble in water but has water permeability, thereby to obtain a constant-rate eluting medicinal tablet. A process of producing such tablet is also disclosed.

6 Claims, 3 Drawing Figures

CONSTANT-RATE ELUTING TABLET AND METHOD OF PRODUCING SAME

DETAILED DESCRIPTION OF THE INVENTION

This invention relates to a constant-rate eluting medicinal tablet and a method of producing such tablet.

The gradually eluting type tablets have many advantages in practical uses such as lessened frequency of medicinal administrations, reduced side effect and prolonged retention of effective concentration of the medicine in blood.

There are known several types of gradually eluting medicinal tablets such as the type availing of the coating film permeability of the medicine, the type dissolved and eluted by the action of digestive enzyme, the type gradually eluted as the tablet absorbs water and is thereby swollen in the alimentary canal and the type eluted under the influence of pH in the digestive canal. However, the first-said type of gradually eluting tablet has the drawbacks that the elution of the medicine is slow to start, that the elution is not constant in rate but takes place in first order elution pattern, and that this type of tablet preparation is unsuited for the medicines which are sparingly soluble in water. Also, the said other types of gradually eluting tablets have a serious disadvantage that their gradual eluting property is greatly affected by the circumstances in the alimentary canal. For these reasons, it was quite difficult in use of the known types of gradually eluting tablets to maintain the effective concentration of the medicine in blood constant.

In an attempt to overcome such difficulty, there was developed a constant-rate eluting device having a fine passage (U.S. Pat. No. 3,845,770). But this device is rather impractical because it requires much time and labor as well as skill for its production; for instance, it is required to drill or punch the fine passage or to embed a fine tube.

The present inventors have made extensive studies in search of a tablet which is free of the above-said defects and, as a result, reached a finding that when a tablet having a hollow or hollows in its surface and containing a water-soluble active component is coated with a coating agent which is insoluble in water but has water permeability, a very small space is formed between the coating film and the hollow surface portion and, quite unexpectedly, this film becomes porous to allow the active principle to elute out at constant rate through this porous film.

This invention was attained on the basis of such finding.

Figure 1:
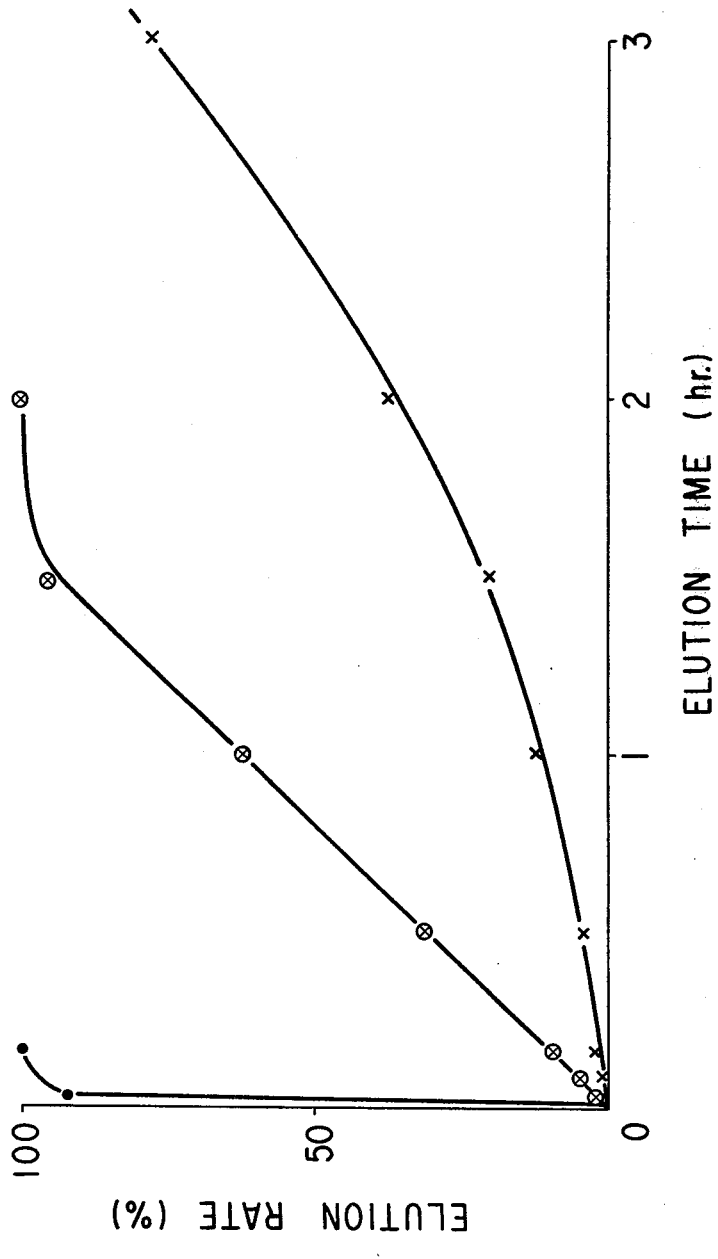
FIG. 1 is a graph showing the relation between elution time and elution rate as described in connection with Example 1 hereinafter.

The surface hollow or recession of the tablet according to this invention is preferably of the following size: 0.1 to 1.0 mm in width, 0.1 to 0.4 mm in depth and greater than 0.1 mm in length, and the area of the hollow portion is preferably less than 1/6 of the overall surface area of the tablet.

It is to be noted that if the width, depth and length are all less than 0.1 mm, the surface hollow portion is perfectly covered with the coating film so that the active principle won't be eluted out from the hollow portion and instead the so-called first order elution takes place. On the other hand, if the recession width is greater than 1.0 mm and the depth is greater than 0.4 mm, the recessed portion is also perfectly covered with the coating film just like the tablet having no recession, and hence, in this case, too, the elution effected is of the first order mode and no constant-rate elution takes place.

The surface recession or hollow may be of any suitable configuration provided that the above-said requirements are met, and the size and number of the hollow may be properly determined by taking into account the size of the tablet, desired rate of elution of the active principle and other factors.

The coating agent used for the tablet of this invention is preferably of the type which is not only insoluble in water and water-permeable but is also soluble in the organic solvents or hydrous organic solvents. To cite some preferred examples of such coating agent, the following may be named: methacrylic acid—methacrylic acid ester copolymers such as Eudragit retard S ®, Eudragit retard L ® (Rohm and Haas) and Eudragit L-S ® (Rohm and Haas), methyl acrylate—methacrylic acid methyl methacrylate copolymers such as MPM-06 ® (Tanabe Pharmaceutical Co., Ltd.), ethyl cellulose, cellulose acetate, polyvinyl acetate, cellulose acetate phthalate and hydroxypropyl cellulose phthalate. As for the tablet constituents, no specific water-soluble excipient is needed if the active principle of the tablet is easily soluble in water, but it is recommendable to use an excipient easily soluble in water, for example saccharoid such as lactose, mannitol, sorbitol, pulverized sucrose, maltose, glucose or the like in case the active principle is difficulty soluble in water. The difficulty water-soluble or water-insoluble excipients usable in this invention include, for example, calcium citrate, calcium phosphate, calcium monohydrogenphosphate, synthetic aluminum silicate and pulverized methacrylic acid—methacrylic acid ester copolymers.

The active principle of the tablet according to this invention may be either of the water-soluble, difficulty water-soluble or water-insoluble type if it is a medicament which is desired to stay in the stomach and intestinal canal for a long time. The following may be cited as examples of the active principle for use in the tablet of this invention: antibiotics such as penicillin, cephalosporin system antibiotics, erythromycins, tetracyclines and macrolide antibiotics; anti-febriles or anodynes such as aspirin, sulpyrine, paraaminoacetophenol, sodium dichlofenac, etc.; antihistamines such as d-chlorophenylamine maleate, diphenylpyrarine, diphenhydramine, etc.; psychotropic drugs such as diazepam, chloropromazine, lithium carbonate, etc.; vitamins; anti-diabetic medicines such as tolubutamide; cardiacs such as prenylamine lactate, digitoxin, etc.; narcotics such as barbituric acid system; diuretics such as sodium salicylate, theobromine, etc.; and anti-malignant tumor agents such as 5-FU. The medicaments usable in this invention are not limited to those cited above.

These substances may be used in suitable combination in the form as they are or after powdered and/or further regulated in grain size according to the purpose of use, and they are molded by a pestle having a convexity according to a normal method to form the tablets with a concave recession or hollow in the surface.

The tablet coating method and other preparation techniques should be suitably selected according to the purpose of use. As the solvent for the coating base, it is recommended to use an alcohol such as methanol, ethanol or isopropyl alcohol, a hydrocarbon chloride such as methylene chloride, methylchloroform or chloroform, or a mixture thereof, or a mixture thereof with water. Such solvent is preferably of the type which is lower than 100° C. in boiling point. The coating thickness may be suitably determined depending on the purpose of use, but usually a thickness within the range of 30 to 150μ is suggested by taking into account the possible break by handling.

If desired, the constant-rate eluting tablet of this invention may be formed into an inner core compressed tablet (generally called inner core tablet) using the tablet of this invention as nucleus, water-soluble film coated tablets or sugar-coated tablets. In this case, by properly prescribing the active principle in the crust constituent, it is possible to provide the "booster dose" so termed in the theory of designing of the gradually eluting tablets.

The invention is now described in further detail by way of some examples thereof.

EXAMPLE 1

6 gr of d-chlorophenylamine maleate, 100 gr of lactose, 11 gr of corn starch and 2 gr of polyvinyl pyrrolidone are mixed together, and this mixture, after further added with 22 ml of ethanol, is kneaded, granulated and dried to obtain granules.

The obtained granules are added with 1.2 gr of magnesium stearate. These granules are then subjected to molding by using a single punch with diameter of 7 mm and curvature of 11 mm and having a convexity measuring 0.5 mm in width, 0.2 mm in depth and 3 mm in length and another single punch with the same dimensions but without said convexity, under the molding pressure of 1,500±50 kg/cm² to form the tablets weighing 120 mg per tablet.

The thus formed tablets are put into a test film coating pan and coated with a coating solution comprising 5 parts of ethyl cellulose having viscosity of 10 cps, 0.5 parts of stearic acid, 1 part of triacetin, 40 parts of isopropyl alcohol and 43.5 parts of chloroform, the coating being completed at the point where the weight of one tablet has become 126 mg on the average.

When the thus prepared tablets were subjected to a disintegration test with a disintegration tester of the Japanese Pharmacopoeia by using the first solution (pH 1.2) according to the enteric tablet test specifications of the Japanese Pharmacopoeia, d-chlorophenylamine maleate was observed eluting out gradually at a constant rate (1.003%/min).

When the same test was conducted on the control tablets with no coating (control sample 1) and those with no concavity (control sample 2), the former completed elution in approximately 3 minutes while the latter showed obvious delay in start of elution and, more typically, the elution was of the primary pattern and also imperfect.

The relation between elution time and elution rate is shown below.

| Time | Products of this invention | Control sample 1 | Control sample 2 |
| --- | --- | --- | --- |
| 2 min. | 2% | 92% | 0% |
| 5 min. | 4% | 100% | 1% |
| 10 min. | 9% | — | 2% |
| 30 min. | 31% | — | 4% |
| 60 min. | 62% | — | 12% |
| 90 min. | 95% | — | 20% |
| 120 min. | 100% | — | 37% |
| 180 min. | — | — | 78% |

This relationship is graphed in FIG. 1. As apparent from the graph, the medicine elutes out at a constant rate in the products of this invention, whereas the elution completes quickly in control sample 1 and the elution pattern is first order and also the elution is imperfect in control sample 2.

EXAMPLE 2

The granules were formed from a mixture of 50 gr of talperisone hydrochloride, 45 gr of lactose, 12 gr of corn starch and 2 gr of polyvinyl pyrrolidone in the same way as Example 1, and these granules were further added with 1.1 gr of magnesium stearate and then molded into the tablets with average weight of 120 mg per tablet by using a single punch with diameter of 7 mm and curvature of 11 and having an inverted V-shaped (acute angle: 60°) convexity with width of 0.2 mm, depth of 0.2 mm and length of 3.5 mm and a similar pestle with no said convexity under the molding pressure of 1,350±50 kg/cm².

The thus formed tablets were then put into a test film coating pan and coated with a coating solution comprising 5 parts of Eudragit retard S ® [methyl & ethyl (methyl) acrylate-trimethyl-metacrylethylammonium chloride copolymer], 1 part of Myvacet ® (distilled acetolated monoghycerides), 74 parts of isopropyl alcohol and 24 parts of acetone, with the coating being completed at the point when each tablet weighed 128 mg on the average.

The thus obtained tablets were subjected to the same test as conducted in Example 1 (by using one tablet for each test).

As a result, in the products of this invention, the medicine eluted out not only in a gradual way but also at a constant rate, whereas in the bare tablets (control sample 1), the medicine was dissolved very quickly while in the tablets with no concavity (control sample 2) the elution was imperfect, not constant and also slow to start. The results are tabulated below.

| Time | Products of this invention | Control sample 1 | Control sample 2 |
| --- | --- | --- | --- |
| 2 min. | 1% | 79% | 0% |
| 5 min. | 3% | 100% | 0% |
| 10 min. | 7% | — | 1% |
| 30 min. | 19% | — | 2% |
| 60 min. | 41% | — | 8% |
| 90 min. | 63% | — | 16% |
| 120 min. | 81% | — | 27% |
| 150 min. | 97% | — | 39% |
| 180 min. | 100% | — | 58% |

Figure 2:
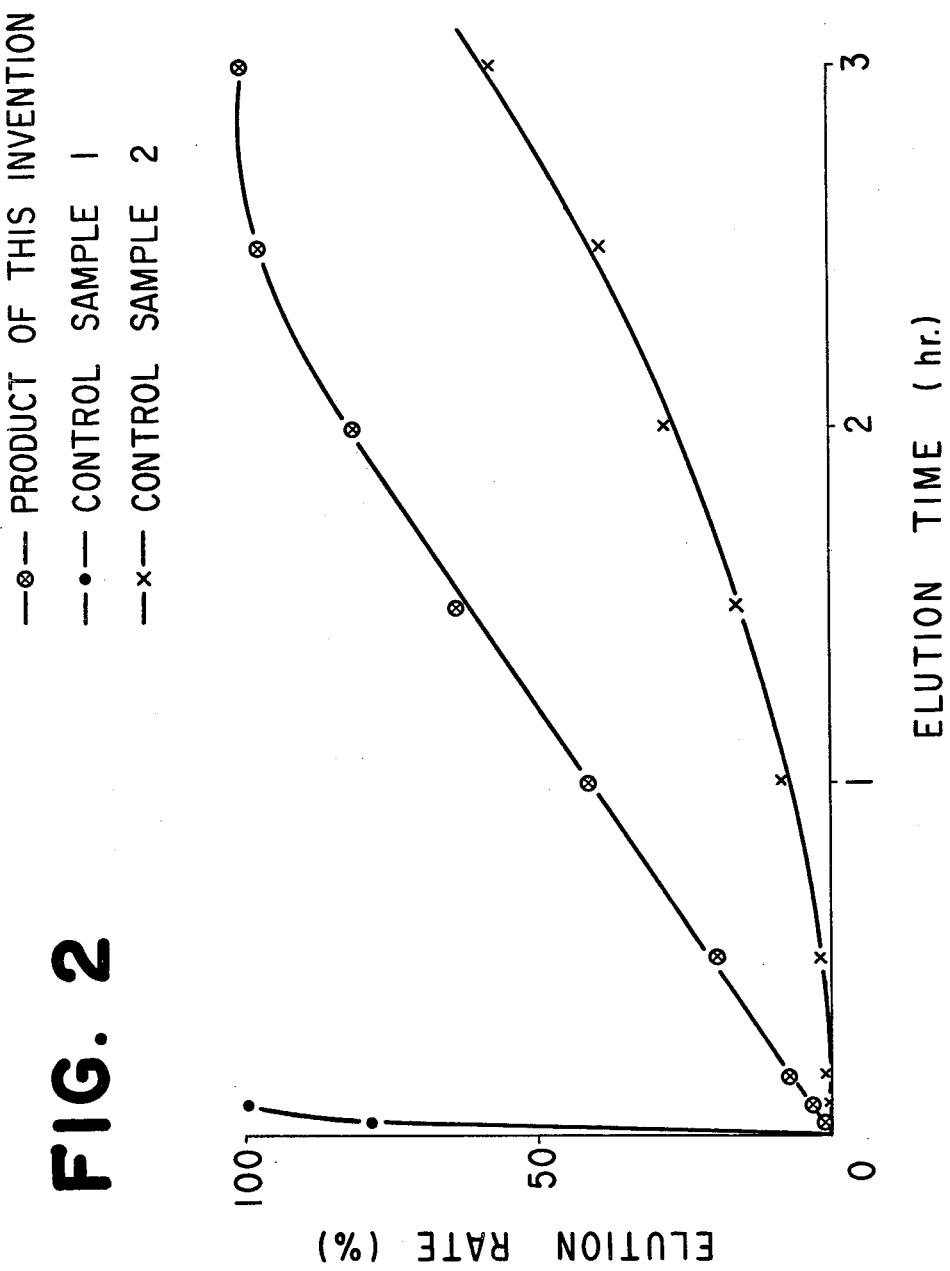
FIG. 2 is a graph showing the relation between elution time and elution rate as described in connection with Example 2 hereinafter.
Figure 3:
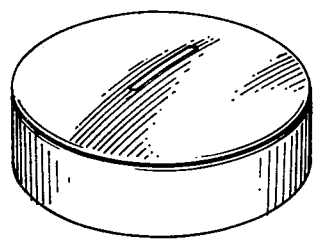
FIG. 3 is a perspective view of a constant-rate eluting tablet produced in accordance with the invention.

The above-shown relation between between elution time and elution rate is graphed in FIG. 2.

EXAMPLE 3

A mixture consisting of 125 gr of finely powdered griseofulvin (specific surface area: 1.52 m$^2$/g; average surface area of body (diameter): approximately 2.7μ), 40 gr of lactose, 7 gr of corn starch and 2 gr of polyvinyl pyrrolidone was granulated by using distilled water, dried and regulated in grain size, followed by further addition of 1.7 gr of magnesium stearate.

Then the thus obtained granules were molded into tablets weighing average 175 mg per tablet by using a single punch with diameter of 8 mm and curvature of 12 mm and having a cruciform convexity measuring 0.4 mm in width, 0.25 mm in depth and 4 mm in length and another similar pestle having no such convexity under the molding pressure of 1,100±50 kg/cm$^2$.

These tablets were then coated with a coating solution same as used in Example 2 until each tablet came to have weight of 183 mg.

When the thus prepared tablets were tested after the manner of Example 1, the products of this invention were gradually swollen with permeation of water and the content medicinal substance was seen effusing out gradually from the hollow portion. Also, measurement of the elution rate showed that although the elution starts somewhat later than the tablets of Examples 1 and 2, such elution proceeds at a constant rate (0.533%/min).

On the other hand, elution occured relatively early in the bare tablets (control sample 1) while, in the case of the tablets with no concavity (control sample 2), almost no substantial elution took place even 300 minutes after start of the test.

The relation between elution time and elution rate in the products of this invention as well as control samples 1 and 2 are shown below.

| Time | Products of this invention | Control sample 1 | Control sample 2 |
| --- | --- | --- | --- |
| 10 min. | 1% | 5% | 0% |
| 20 min. | 6% | 9% | 0% |
| 30 min. | 11% | 15% | 0% |
| 60 min. | 26% | 39% | 1% |
| 120 min. | 60% | 82% | 1% |
| 180 min. | 92% | 100% | 2% |
| 240 min. | 100% | — | 2% |
| 300 min. | — | — | 4% |

EXAMPLE 4

Granules are prepared from a mixture of 25 gr of sodium diclofenac, 80 gr of mannitol, 17 gr of corn starch and 2 gr of hydroxypropyl cellulose by using distilled water, and the formed granules are dried and regulated in grain size, followed by addition of 1 gr of magnesium stearate.

The thus obtained granules are then molded into tablets weighing 125 mg per tablet by using a singly punch with diameter of 8 mm and curvature of 12 mm and having a circular convexity 0.3 mm in diameter and 0.3 mm in depth and another single punch with no such convexity under the molding pressure of 1,300±50 kg/cm$^2$, and the formed tablets are coated with a coating solution same as used in Example 1 until the weight of each tablet becomes 133 mg. When the thus prepared tablets were subjected to the same test as Example 1, the content of medicinal substance was seen effusing out at a constant rate (1,467%/min) from the hollow portion of each tablet tested of this invention.

On the other hand, the bare tablet (control sample 1) was very quick to elute while the tablet with no hollow (control sample 2) gave only 20% elution even 240 minutes after start of the test. The results are tabulated below.

| Time | Products of this invention | Control sample 1 | Control sample 2 |
| --- | --- | --- | --- |
| 10 min. | 13% | 32% | — |
| 20 min. | 29% | 88% | — |
| 30 min. | 45% | 100% | — |
| 40 min. | 58% | — | — |
| 50 min. | 74% | — | — |
| 60 min. | 88% | — | 4% |
| 90 min. | 100% | — | 5% |
| 120 min. | — | — | 8% |
| 180 min. | — | — | 14% |
| 240 min. | — | — | 20% |

EXAMPLE 5

30 mg (Potency) (14.5 mg in weight) of bleomycin hydrochloride, 140 mg of calcium citrate and 0.5 mg of magnesium stearate are mixed and this mixture is molded into tablets weighing 155 mg per tablet by using a 10×4 mm rectangular pestle having an inverted V-shaped convexity with acute angle of 60°, width of 0.2 mm, depth of 0.2 mm and straight line portion length of 2 mm under the molding pressure of 980±50 kg/cm$^2$.

Then the thus formed tablets are coated with a coating solution same as used in Example 3 until each table has weight of 183 mg.

When the test of Example 1 was conducted on the thus prepared tablets by using a phosphate buffer with pH 6.8 as eluent, the tablets of this invention induced elution of the medicine at a constant rate (8.5%/hr) from the hollow portion of the tablet. Whereas in the bare tablet (control sample), the elution occured very quickly and was completed in 30 minutes. The results are tabulated below.

| Time | Products of this invention | Control sample |
| --- | --- | --- |
| 30 min. | 6% | 100% |
| 1 hr. | 10% | — |
| 2 hr. | 18% | — |
| 4 hr. | 36% | — |
| 6 hr. | 49% | — |
| 8 hr. | 67% | — |
| 10 hr. | 83% | — |

What is claimed is:

1. A method of producing a constant-rate eluting tablet comprising the steps of molding a medicinal composition containing a water-soluble substance or substances with a pestle having a convexity or convexities to form a tablet having a hollow or hollows, and then coating this tablet with a coating agent which is insoluble in water but has water permeability, said hollow measuring 0.1 to 1.0 mm in width, 0.1 to 0.4 mm in depth and greater than 0.1 mm in length, and as for the area less than 1/6 of the overall surface area of the tablet, wherein the coating agent insoluble in water but having water permeability is a methacrylic acid—methacrylic acid ester copolymer, ethyl cellulose, cellulose acetate, polyvinyl acetate, cellulose acetate phthalate or hydroxypropyl cellulose phthalate, and wherein the coating thickness is within the range of 30 to 150μ.

2. A constant-rate eluting tablet made in accordance with the method of claim 1 by coating a bare tablet having a hollow or hollows in its surface and containing a water-soluble component with a coating agent which is insoluble in water but has water permeability, said hollow measuring 0.1 to 1.0 mm in width, 0.1 to 0.4 mm in depth and greater than 0.1 mm in length, and as for the area less than 1/6 of the overall surface area of the tablet, wherein the coating agent insoluble in water but having water permeability is a methacrylic acid—methacrylic acid ester copolymer, ethyl cellulose, cellulose acetate, polyvinyl acetate, cellulose acetate phthalate or hydroxypropyl cellulose phthalate, and wherein the coating thickness is within the range of 30 to 150μ.

3. A constant-rate eluting tablet of claim 1, wherein the water-soluble component is a water-soluble medicine.

4. A constant-rate eluting tablet of claim 1, wherein the water-soluble material is composed of a water-soluble medicine and a water-soluble excipient.

5. A constant-rate eluting tablet of claim 1, wherein the water-soluble component consists of a water-soluble medicine and a difficultly water-soluble or water-insoluble excipient.

6. A constant-rate eluting tablet of claim 1, wherein the water-soluble component consists of a difficultly water-soluble or water-insoluble medicine and a water-soluble excipient.

* * * * *